United States Patent [19]

Bitter et al.

[11] Patent Number: 4,898,690
[45] Date of Patent: Feb. 6, 1990

[54] BUBBLE-BATH CONCENTRATE GEL

[75] Inventors: Ingrid Bitter; Wolfhard Scholz, both of Krefeld; Werner Schneider, Krefeld-Bockum, all of Fed. Rep. of Germany

[73] Assignee: Henkel Kommanditgesellschaft auf Aktien, Duesseldorf, Fed. Rep. of Germany

[21] Appl. No.: 187,108

[22] Filed: Apr. 28, 1988

[30] Foreign Application Priority Data

Apr. 30, 1987 [DE] Fed. Rep. of Germany ....... 3714455

[51] Int. Cl.$^4$ ............................. C11D 1/14; C11D 1/12
[52] U.S. Cl. ..................................... 252/554; 252/533; 252/DIG. 1; 252/174.22; 252/174.21; 252/174.11; 252/DIG. 5
[58] Field of Search ............... 252/535, 549, 533, 554, 252/DIG. 1, 174.21, 174.22, 174.11, DIG. 5

[56] References Cited

U.S. PATENT DOCUMENTS

| | | | |
|---|---|---|---|
| 4,130,497 | 12/1978 | Oneto et al. | 252/89 |
| 4,371,548 | 2/1983 | Herman et al. | 424/365 |
| 4,426,310 | 1/1984 | Pierre Verunica | 252/106 |

FOREIGN PATENT DOCUMENTS 0167382 1/1986 European Pat. Off. .

OTHER PUBLICATIONS

Brookfield Engineering Labororaties, Inc. (catalog, 1987), pp. 2, 3, 6, 7.

Primary Examiner—Paul Lieberman
Assistant Examiner—John F. McNally
Attorney, Agent, or Firm—Ernest G. Szoke; Wayne C. Jaeschke; Norvell E. Wisdom

[57] ABSTRACT

Bubble-bath foam concentrate compositions showing high structural viscosity and good solubility in water contain 35 to 45% by weight alkyl ether sulfate surfactants, 5 to 15% by weight nonionic polyglycolether surfactants, 1 to 5% by weight of one or more amphoteric or zwitterionic surfactants, 1 to 5% by weight glycerol polyglycol ether monofatty acid esters or fatty acid mono- or diglyceride polyglycol ethers, 2 to 10% by weight of a water-insoluble perfume oil and 30 to 50% by weight water. The compositions have a gel-like appearance and show high foaming power and high compatability with the skin. The combination of the compositions with suitable dispensing containers and a method for using such compositions to provide bubble-baths.

10 Claims, No Drawings

BUBBLE-BATH CONCENTRATE GEL

BACKGROUND OF THE INVENTION

1. Field of the Invention

This invention relates to a gel-form foam bubble bath concentrate of high surfactant and perfume content.

2. Statement of Related Art

Bubble bath preparations are added to bath water to produce a voluminous, fine-bubbled foam, to give the bath water a pleasant odor, and to assist cleansing of the body in the bath water without the skin being harmed by an excessive deoiling effect of the surfactants. Accordingly, it has often been proposed to introduce suitable additives, such as cosmetic oil components, reoiling or moisturizing agents, water soluble proteins, or protein degradation products, not only to counteract the deoiling effect of the surfactants, but also to obtain a cosmetic improvement in the condition of the skin.

Standard commercial products contain 10 to 30% by weight washing-active substance and are used in doses of 20 to 40 g for a full bath (approx. 200 l). Products having a relatively high concentration of washing-active substance have the advantage of lower packaging costs, lower preservative demand and less expensive storage. However, there are also highly concentrated and even anhydrous products which are attended by numerous disadvantages.

U.S. Pat. No. 4,371,548 and corresponding German patent document 29 43 202 describe foam bath preparations containing 20 to 80% by weight surfactants and 20 to 80% by weight cosmetic oils. U.S. Pat. No. 4,130,497 and corresponding German patent document 27 00 891 also describe bath additives containing 40 to 75% by weight surfactants and 15 to 50% by weight cosmetic oils. The object of the high surfactant content of these products is largely to solubilize the cosmetic oils or to make them dispersible in water. However, the products are not satisfactory in their foaming power and leave noticeably oily residues behind on the skin. Other highly concentrated surfactant compositions have the disadvantage that they are either stiff pastes or form poorly soluble, solid gel particles on attempted dissolution in water, which is partially overcome by the addition of solvents or solubilizers.

DESCRIPTION OF THE INVENTION

Other than in the operating examples, or where otherwise indicated, all numbers expressing quantities of ingredients or reaction conditions used herein are to be understood as modified in all instances by the term "about".

The present invention provides foam bath concentrates which, on the one hand, generate a rich foam, solubilize large amounts of perfume oil and do not have a harmful effect on the skin or leave behind an unpleasant oily film on the skin and, on the other hand, dissolve easily and quickly in the bath water. This is achieved in large measure by the foam bath concentrate according to the invention which comprises:

(A) 35 to 45 (preferably 35 to 40)% by weight of one or more alkyl ether sulfate surfactants of the formula $R^1-O(C_2H_4O)_n-SO_3Na$, in which $R^1$ is a $C_{12-16}$ alkyl and n is 1 to 6;

(B) 5 to 15 (preferably 6 to 14)% by weight of one or more nonionic polyglycol ether surfactants of the formula $R^2-A-(C_2H_4O)_x-H$ in which $R^2$ is a $C_{12-18}$ alkyl, alkenyl or acyl, A is oxygen or $-NH-$, and x is 3 to 9;

(C) 1 to 5 (preferably 2 to 4)% by weight of one or more amphoteric or zwitterionic surfactants;

(D) 1 to 5 (preferably 2 to 4)% by weight of one or more glycerol polyglycol ether monofatty acid esters or fatty acid mono- or diglyceride polyglycol ethers, based on a $C_{12-18}$ fatty acid containing 5 to 20 glycol ether moieties in either case;

(E) 2 to 10 (preferably 4 to 6)% by weight of one or more water-insoluble perfume oils; and (F) the balance q.s. to 100% by weight of water; all percentages being based upon the total weight of the concentrate composition.

The inventive balanced composition of highly concentrated alkyl ether sulfate, nonionic surfactant, amphoteric or zwitterionic surfactant and hydrophilic oil gives liquid bath additives which, by virtue of their high structural viscosity, appear to be gels, or at least create a gel-like impression. This means that the (thixotropic) foam bubble-bath concentrates according to the invention appear very highly viscous and nonfree-flowing, but in fact flow very freely under the effect of shear forces and may be expressed without difficulty from flexible bottles or may readily be dispensed from plunger-type or manual pressure-differential dispensers. This invention therefore encompasses the combination of the gel-like compositions disclosed herein contained in the foregoing containers (which normally cannot dispense a gel-like substance). The invention also encompasses using the combination to dispense a bubble-bath effective amount of concentrate, and mixing it with bathing water prior to taking a bath. In addition, the foam bath concentrates according to the invention dissolve quickly in bath water without colloidal gel formation and provide for a stable, uniform distribution of the perfume oils and the dyes. The skin is gently cleansed so that the skin care components, if any, present in the preparation fully develop their effect.

(A) Alkyl ether sulfate surfactants corresponding to the formula $R^1-O(C_2H_4O)_n-SO_3Na$ are known commercial products. They are prepared form $C_{12-16}$ fatty alcohols preferably having a linear alkyl chain by addition of 1 to 6 mols ethylene oxide and sulfation of the obtained ethoxylates with sulfur trioxide or chlorosulfonic acid. The resulting sulfuric acid semiesters of the fatty alcohol ethoxylates are then neutralized with aqueous sodium hydroxide. Because of the necessary high concentration of alkyl ether sulfate surfactant in the product, 60 to 70% by weight free-flowing to gel-form solutions rather than the standard commercial 25 to 30% by weight aqueous solutions may be used for this purpose. Products such as these are commercially available (for example Texapon TM N70, a product of Henkel KGaA).

(B) Nonionic polyglycol ether surfactants corresponding to the formula $R^2-A-(C_2H_4O)_x-H$ are also commercially available products. They are prepared by the addition of 3 to 9 mol ethylene oxide (i.e. x is 3 to 9) onto saturated and unsaturated fatty alcohols, fatty amines and/or fatty acid amides containing 12 to 18 carbon atoms or by the addition of 2 to 8 mol ethylene oxide onto fatty acid ($C_{12-18}$) monoethanolamides.

(C-1) Ampoteric surfactants useful are those which, in addition to a $C_{12-18}$ alkyl or acyl, contain an amino and a carboxylic or sulfonic acid moiety in the molecule. Examples of amphoteric surfactants are N-($C_{12-18}$)-β-aminopropionic acid, N-($C_{8-18}$-alkyl)-β- aminobutyric acid, N-($C_{8-18}$-alkyl)-iminodiacetic acid, N-($C_{12-16}$-alkyl)-N-2-hydroxyethylglycine, N-($C_{12-18}$-alkyl)taurine, N-$C_{8-18}$-alkylbenzylamine-p-sulfonic acid, and N-($C_{8-18}$-alkyl)-1-amino-butane-3-sulfonic acid.

(C-2) Zwitterionic surfactants useful are those which, in addition to a $C_{12-18}$ alkyl or acyl, contain a quaternary ammonium and a carboxylate or sulfonate in the molecule. Examples of zwitterionic surfactants are N-($C_{8-18}$-alkyl)-N,N-dimethyl ammonioglycinate, N-coconutacylamidopropyl-N,N-dimethyl ammonioglycinate, N-($C_{8-18}$-alkyl)-N-2-hydroxyethyl-N-methyl-β-ammonionpropionate, and N-($C_{8-18}$-alkyl)-N,N-dimethyl-β-ammniopropanesulfonate.

(D) Glycerol polyglycol ether monofatty acid esters useful are hydrophilic oil components which reoil the skin. Products of this structure are known from the literature, [see published German patent application 20 24 051], and are commercially available, under the trademark Cetiol ™ HE (a product of Henkel KGaA). Fatty acid mono- or diglyceride polyglycol ethers are also known from the literature as reoiling components, [see U.S. Pat. No. 2,617,754 and published German patent application 14 67 816].

(E) The combination of ingredients (A), (B), (C) and (D) in the quantities specified is suitable for clearly dissolving (E) 2 to 10% by weight water-insoluble perfume oils and, on dissolution in (F) water, of homogeneously dispersing all ingredients in the water without impairing either the desired foam or the desired pleasant feeling on the skin. Etheral oils and synthetic perfumes suitable for the perfuming of personal hygiene preparations and mixtures of these substances may be used as the water-insoluble perfume oils.

(G) In addition to the above required ingredients, the inventive foam bath concentrate compositions may also contain standard auxiliaries, and/or additives for bubble-bath concentrates in relatively small quantities of 0 to 5, preferably 0.1 to 3% by weight of the total composition. Useful auxiliaries and additives include: Citric acid, preservatives, dyes, electrolytes (for example sodium chloride, magnesium sulfate), polyethylene glycols, cationic polymers, vitamins, plant extracts and other known skin-cosmetic agents.

In manufacturing the inventive compositions, the water soluble components may be added together with the water or last of all. Oil soluble components should be dissolved together with the perfume oil in a mixture of ingredients (B) and (D).

Of above-mentioned ingredients (A), (B), (C) and (D), special products or product groups are particularly suitable for combination with one another and for production of foam bath concentrates according to the invention which show optimal properties in regard to their performance properties and particularly in regard to their foaming power, their compatibility with the skin and their dissolvability in water. One such particularly preferred embodiment of the invention is a foam bath concentrate comprising:

(A) 35 to 40% by weight of an alkyl ether sulfate surfactant corresponding to the formula $R^1$—O($C_2H_4O$)$_n$—$SO_3Na$, in which $R^1$ is a $C_{12-16}$ alkyl and n is 1 to 3;

(B)-1 2 to 6% by weight of a nonionic polyglycol ether surfactant corresponding to the formula $R^2$—O—($C_2H_4O$)$_x$—H, in which $R^2$ is a $C_{16-18}$ alkyl or alkenyl and x is 3 to 6;

(B)-2 4 to 8% by weight of a nonionic polyglycol ether surfactant corresponding to the formula $R^3CONH(C_2H_4O)_x$—H, in which $R^3CO$ is a $C_{12-18}$ acyl and x is 3 to 6;

(C2) 2 to 4% by weight of a zwitterionic surfactant corresponding to the formula $R^3CONH$-$(CH_2)_3$—$N^{(+)}(CH_3)_2CH_2COO^{(-)}$, in which $R^3CO$ is a $C_{12-18}$ acyl;

(D) 2 to 4% by weight of a fatty acid ($C_{12-18}$) monoester of an adduct of 7-10 mol ethylene oxide with glycerol;

(E) 4 to 6% by weight of a water-insoluble perfume oil; and (F) 35 to 45% (i.e. q.s. to 100%) by weight water.

The foam bath concentrates according to the invention may readily be prepared by mixing the ingredients at room temperature, i.e. without the need for heating. However, it is advantageous to keep to a certain order in the mixing of the ingredients. The formation of poorly soluble gel-form particles is avoided in this way. Furthermore, in this manner the ingredients are rapidly and homogeneously mixed. Preferably, ingredients (B) and (D) are introduced first; the perfume oil (E) dissolved therein; and ingredients (C) and (F), and, finally, ingredient (A) successively added and homogeneously incorporated in the mixture with stirring.

The foam bath concentrates according to the invention show high structural viscosity and appear gel-like, but may readily be stirred, pumped, packed and emptied from containers under the influence of shear forces. The viscosity of the products is normally 10 to 40 Pa.s (preferably 10 to 25 Pa.s) (20° C.), as measured with a Haake type RV3 Rotovisco ™ rotational viscosimeter, MV2 measuring system at 0.4 to 1 r.p.m. [a Pascal second (Pa.s)] is approximately equal to 1000 centipoise.

The following Examples are intended to illustrate the invention without limiting it in any way.

EXAMPLES

Gel-form foam bath concentrate compositions

| | Ingredients | Examples 1 | Examples 2 |
|---|---|---|---|
| (A) | Texapon ™ N70 | 52% by weight[a] | 57% by weight[b] |
| (B) | Eumulgin ™ 05 | 5% by weight | 3% by weight |
| (B2) | Eumulgin ™ C4 | 5% by weight | 7% by weight |
| (C) | Dehyton ™ K | 2.5% by weight[c] | 3.5% by weight[d] |
| (D) | GOF* | 2.5% by weight | 3.5% by weight |
| (E) | Perfume oil | 5% by weight | 5% by weight |
| (G) | Citric acid.H2O | 0.13% by weight | 0.13% by weight |
| (F) | Water | ad 100% by weight | ad 100% by weight |
| Test Results | | | |
| | Appearance | opaque gel | opaque gel |
| | Viscosity | 12 [Pa.s] | 24 [Pa.s] |

-continued

| | Examples | |
|---|---|---|
| Ingredients | 1 | 2 |
| (20° C.)# | | 5 |

Notes:
Haake RV3 Rotovisco ™, MV2 measuring system, ribbed, 1 r.p.m.)
*GOF: glycerol ethoxylate fatty acid ester (coconut oil fatty acid monoester of an adduct of 7 mol ethylene oxide with glycerol)
Texapon ™ N70: 70% aqueous solution of an alkyl ether sulfate sodium salt based on an adduct of 2 mol ethylene oxide with a linear $C_{12-14}$ fatty alcohol mixture (70:30)
Eumulgin ™ C4: an adduct of 4 mol ethylene oxide with coconut fatty acid ($C_{12-18}$) monoethanolamide
Eumulgin ™ 05: an adduct of 5 mol ethylene oxide with an oleylcetyl alcohol mixture
Dehyton ™ K: a 30% aqueous solution of an N—coconutacylaminopropyl-N,N—dimethyl ammonium glycinate.
(a)70% by weight aqueous solution, 36.4% by weight active ingredient.
(b)70% by weight aqueous solution, 39.9% by weight active ingredient.
(c)30% by weight aqueous solution, .75% by weight active ingredient.
(d)30% by weight aqueous solution, 1.05% by weight active ingredient.

As can be seen from the above, two compositions according to this invention, but differing as to the parameters of the ingredients, both had the appearance of opaque gels. However, when subjected to the shearing force of a rotary-type viscometer, the measured viscosities were, respectively, only 12 and 24 Pascal seconds. That this is contrary to normal expectations may be seen from page 7 of the Brookfield Engineering Laboratories, Inc. catalogue (1987). "Gels" are listed therein only under the heading "high viscosity" along with asphalt, molasses, peanut butter, and paste, for which minimum viscosities of 200 and 800 are given. Viscosities as measured above (i.e. 12 and 24 Pa.s) all fall under the heading "low viscosity" or, to a degree, "medium viscosity". It may be noted that "low viscosity" has typical applications of latex, oils, solvents, soups, and the like; and "medium viscosity" has typical application of creams, inks, paints, surface coatings and toothpaste. This demonstrates that substances having the above indicated and claimed viscosities of this invention, would not be expected to exhibit gel-like appearances before being subjected to shearing forces. Texapon ™ N 70, Eumulgin ™ C 4, Eumulgin ™ 05 and Dehyton ™ K are trademarks of HENKEL KGaA, Düsseldorf, Germany.

We claim:

1. A bubble-bath concentrate gel composition consisting essentially of:
   (A) about 35 to 45% by weight of one or more alkyl ether surfactants of the formula $R^1$-O$(C_2H_4O)_n$-SO$_3$Na, in which $R^1$ is a $C_{12-16}$ alkyl and n is 1 to 6;
   (B) about 5 to 15% by weight of one or more nonionic polyglycol ether surfactants of the formula $R^2$-A-$(C_2H_4O)_x$-H, in which $R^2$ is a $C_{12-18}$ alkyl, alkenyl or acyl, A is oxygen or -NH-, and x is 3 to 9;
   (C) about 1 to 5% by weight of one or more amphoteric or zwitterionic surfactants;
   (D) about 1 to 5% by weight of one or more glycerol polyglycol ether monofatty acid esters or of fatty acid mono-acid or diglyceride polyglycol ethers based on a $C_{12-18}$ fatty acid containing 5 to 20 glycol ether moieties in either case;
   (E) about 2 to 10% by weight of a water-insoluble perfume oil;
   (F) water q.s. to 100% by weight; and
   (G) 0 to about 5% by weight of standard auxiliaries, additives and mixtures thereof for bubble bath concentrates;
   all percentages based upon the concentrate as a whole.

2. The composition of claim 1 wherein:
   (A) is present in about 35 to 40%;
   (B) is present in about 6 to 14%;
   (C) is present in about 2 to 4%;
   (D) is present in about 2 to 4%; and
   (E) is present in about 4 to 6%;
   all percentages being by weight based upon the total composition.

3. The composition of claim 1 wherein:
   (A) has a formula in which n is 2 to 3;
   (B) has a formula in which $R^2$ is a $C_{16-18}$ alkyl and x is 3 to 6; or $R^2$ is a $C_{12-18}$ acyl and x is 3 to 6; or a mixture thereof;
   (C) is a zwitterionic surfactant of the formula $R^4$CONH-$(CH_2)_3$—N$(CH_3)_2$ in which $R^4$CO is a $C_{12-18}$ alkyl; and
   (D) is a fatty acid ($C_{12-18}$) monoester of an adduct of 7 to 10 mol ethylene oxide with glycerol.

4. The composition of claim 1 consisting essentially of:
   (A) 35 to 40% by weight of an alkyl ether sulfate surfactant corresponding to the formula $R^1$—O$(C_2H_4O)_n$—SO$_3$Na, in which $R^1$ is a $C_{12-16}$ alkyl and n is 2 to 3;
   (B)-1 2 to 6% by weight of a nonionic polyglycol ether surfactant of the formula $R_2$NH$(C_2H_4O)_x$—H, in which $R^2$ is a $C_{6-18}$ alkyl or alkenyl and x is 3 to 6;
   (B)-2 4 to 8% by weight of a nonionic polyglycol ether surfactant of the formula $R_2$NH$(C_2H_4O)_x$-H, in which $R_2$ is a $C_{6-18}$ acyl and x is 3 to 6;
   (C) 2 to 4% by weight of a zwitterionic surfactant of the formula $R^3$CONH$(CH_2)_3$-N$(CH_3)_2$CH$_2$COO(−), in which $R^4$CO is a $C_{12-18}$ acyl;
   (D) 2 to 4% by weight of a fatty acid ($C_{12-18}$) monoester of an adduct of 7 to 10 mol ethylene oxide with glycerol;
   (E) 4 to 6% by weight of a water-insoluble perfume oils;
   (F) water q.s. to 100% by weight; and
   (G) 0 to about 5% by weight of standard auxiliaries and/or additives for bubble-bath concentrates;
   all percentages based upon the concentrate as a whole.

5. The composition of claim 1 wherein (G) is present and is at least one preservative, dye, electrolyte, polyethylene glycol, cationic polymer, vitamin, or plant extract.

6. The composition of claim 2 wherein (G) is present and is at least one preservative, dye, electrolyte, polyethylene glycol, cationic polymer, vitamin, or plant extract.

7. The composition of claim 3 wherein (G) is present and is at least one preservative, dye, electrolyte, polyethylene glycol, cationic polymer, vitamin, or plant extract.

8. The composition of claim 4 wherein (G) is present and is at least one preservative, dye, electrolyte, polyethylene glycol, cationic polymer, vitamin, or plant extract.

9. The combination of the composition of claim 1 contained in a flexible tube, flexible bottle, or manual pressure differential dispenser.

10. A method for preparing a bubble-bath comprising using the combination of claim 9 to dispense a bubble-bath effective amount of said concentrate gel and mixing the dispensed concentrate gel with bath water prior to taking a bath.

* * * * *